US00PP30714P2

(12) United States Plant Patent
MacGregor et al.

(10) Patent No.: US PP30,714 P2
(45) Date of Patent: Jul. 16, 2019

(54) ***ANEMONE* PLANT NAMED 'MACANE002'**

(50) Latin Name: ***Anemone* hybrid**
Varietal Denomination: MACANE002

(71) Applicants: Elizabeth MacGregor, Kirkcudbright (GB); Alasdair MacGregor, Kirkcudbright (GB)

(72) Inventors: Elizabeth MacGregor, Kirkcudbright (GB); Alasdair MacGregor, Kirkcudbright (GB)

( * ) Notice: Subject to any disclaimer, the term of this patent is extended or adjusted under 35 U.S.C. 154(b) by 0 days.

(21) Appl. No.: 15/932,991

(22) Filed: Jun. 5, 2018

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A distinct new cultivar of *Anemone* plant named 'MACANE002', characterized by early flowering, and clump forming plants. Flowers have a distinct darker lavender and purple coloration on the underside of petals. The new cultivar is an *Anemone* typically suited for ornamental container and landscape use.

2 Drawing Sheets

Figure 1:
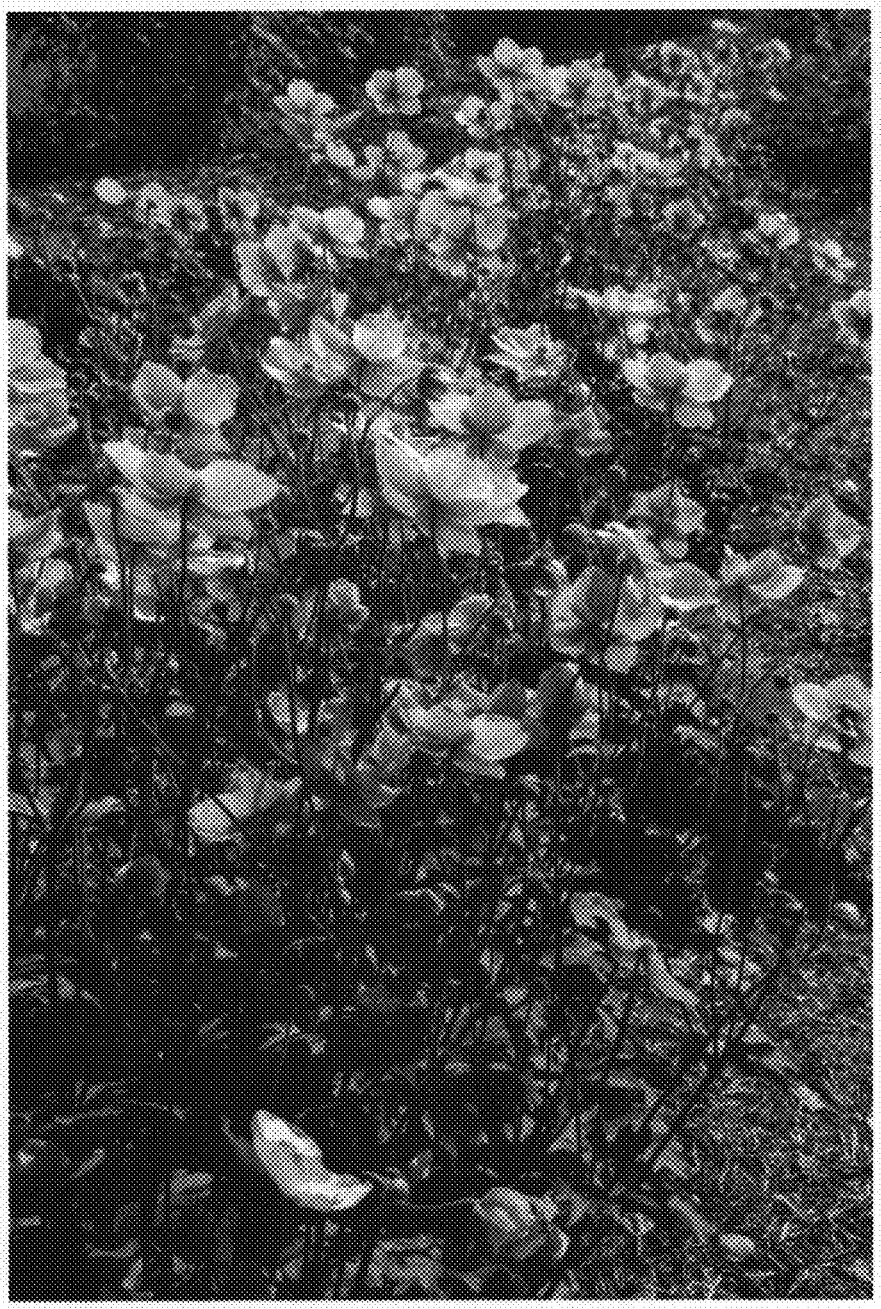

Latin name of the genus and species: *Anemone* hybrid.
Variety denomination: 'MACANE002'.

BACKGROUND OF THE INVENTION

The new *Anemone* was discovered by the inventors, Elizabeth and Alasdair MacGregor, as part of a breeding program, using *Anemone* hybrids as parents. The seed parent is an unpatented, proprietary *Anemone* hybrid which was the result of a crossing of the unpatented *Anemone hybrida* 'Pamina' and an unnamed *Anemone rupicola*. The pollen parent is the unpatented *Anemone hybrida* 'Rosenschale'. The cross was made in 2005, and the selection of the new variety made during 2007. at a commercial nursery, in Kirkcudbright, Scotland.

Asexual reproduction was first performed by root cuttings in 2008, at the same commercial nursery Kirkcudbright, Scotland. Plants produced have proved to be stable and reproduced true to type in successive generations. During the long testing period to determine stability of the new selection, plant material was kept in a confidential location and not available to the public. Plant material was made available to the public by during June of 2017, from plants made available to a third party directly by the inventors.

SUMMARY OF THE INVENTION

The cultivar 'MACANE002' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MACANE002'. These characteristics in combination distinguish 'MACANE002' as a new and distinct *Anemone* cultivar:

1. Earlier flowering than typical *Anemone hybrida* cultivars considered of the Japanese *Anemone* category.
2. Distinct darker lavender and purple coloration on reverse of petals.
3. Clump forming plants, rather than the typical running habit of *Anemone hybrida* cultivars considered of the Japanese *Anemone* category.

PARENTAL COMPARISON

Plants of the new cultivar 'MACANE002' are similar to the seed parent in most horticultural characteristics. However, plants of 'MACANE002' differ in the following:

1. The seed parent has white flowers with a lilac-blue petal underside. The new variety has light lavender flowers with purple veins and a darker center blush. Petals undersides are colored darker lavender with a darker purple flush.

Plants of the new cultivar 'MACANE002' are similar to the pollen parent in most horticultural characteristics. However, plants of 'MACANE002' differ in the following:

1. The pollen parent has deep pink flowers, with the same petal color both upper and underside. The new variety has light lavender flowers with purple veins and a darker center blush. Petals undersides are colored darker lavender with a darker purple flush.
2. The pollen parent has a running plant habit, the new variety is clump forming.

COMMERCIAL COMPARISON

Plants of the new cultivar 'MACANE002' are similar to the known commercial variety, *Anemone hybrida* 'MACANE007', U.S. Plant Pat. No. 27,383, in some horticultural characteristics. However, plants of 'MACANE002' differ in the following:

1. The new variety has single flowers rather than semi-double.

2. The new variety has light lavender flowers with purple veins and a darker center blush. Petals undersides are colored darker lavender with a darker purple flush. This comparator has white flowers with lilac-blue reverse.

Plants of the new cultivar 'MACANE002' are similar to the known commercial variety, *Anemone hybrida* 'MACANE004', U.S. Plant Pat. No. 27,384 in some horticultural characteristics. However, plants of 'MACANE002' differ in the following:

1. The new variety has single flowers rather than semi-double.
2. The new variety has light lavender flowers with purple veins and a darker center blush. Petals undersides are colored darker lavender with a darker purple flush. This comparator has white flowers with lilac-blue reverse.

BRIEF DESCRIPTION OF THE PHOTOGRAPHS

The accompanying photograph in FIG. 1 illustrates in full color a typical plants of 'MACANE002' grown outdoors in a garden in Kirkcudbright, Scotland. This plant is approximately 15 months old.

Figure 2:
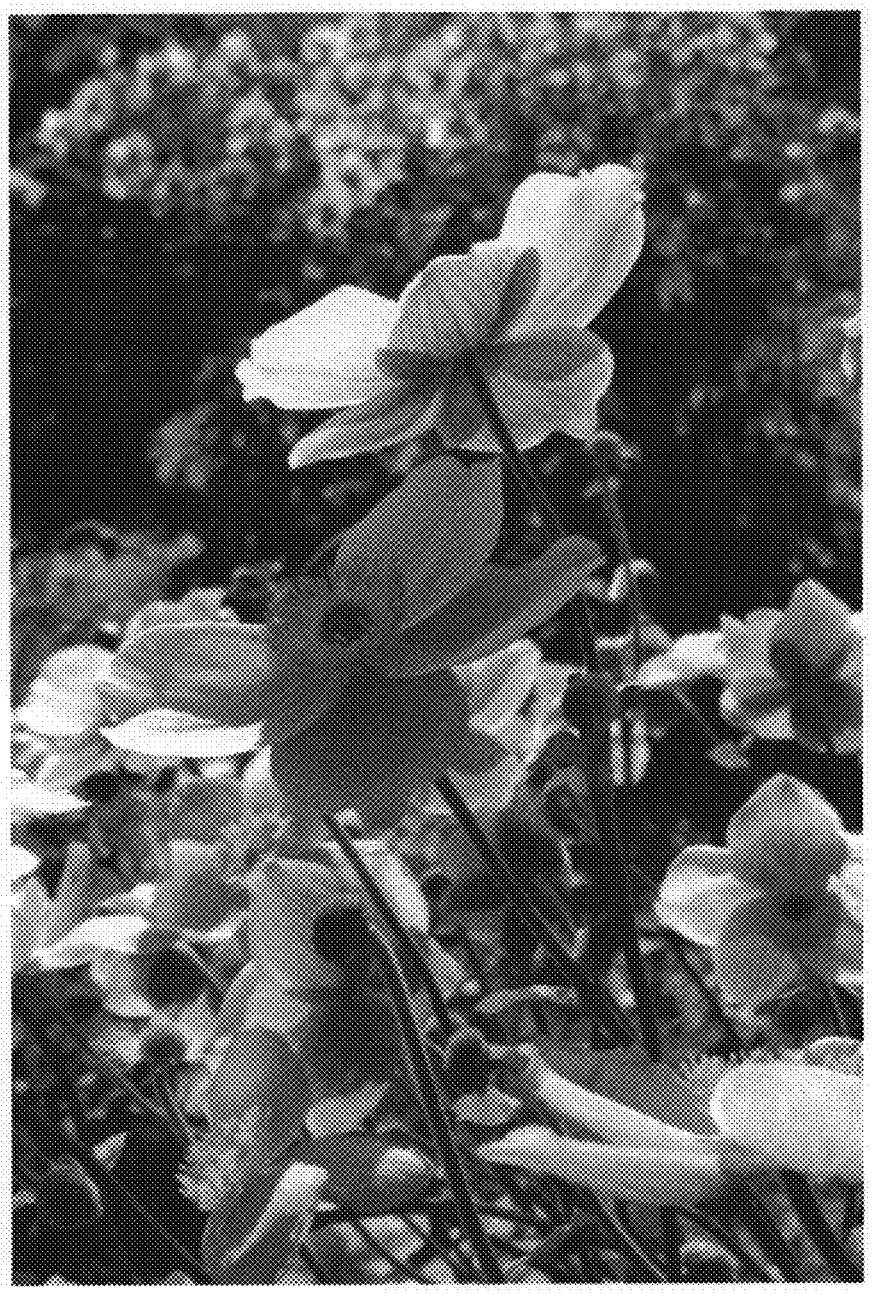

FIG. 2 illustrates a close up of the flower, showing upper and lower petal coloration.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'MACANE002' plants grown outdoors in Kirkcudbright, Scotland at a commercial nursery. The growing temperature ranged from 0° C. to 12° C. at night to 8° C. to 22° C. during the day. During the winter period December to March, plants were sheltered in a large poly-tunnel with day temperatures ranging from 5° C. to 18° C., and night temperatures ranging from −5° C. to 8° C. No artificial light, photoperiodic treatments or chemical treatments were given to the plants. Measurements and numerical values represent averages of typical flowering types.

Botanical classification: *Anemone* hybrid 'MACANE002'.

Age of the plant described: Approximately 15 months.

Container size of the plant described: 2 liter commercial container.

PROPAGATION

Time to produce a flowering plant from root-cutting: Nine to twelve months.

Root description: Fibrous, reddish-brown (not R.H.S. identified) in color.

Rooting habit: Dense, freely branching.

PLANT

Growth habit: Upright, clump forming flowering perennial.

Pot size of plant described: 2 liter circular pot (14 cm).

Height: 25 cm.

Plant spread: 25 cm.

Growth rate: Moderate.

Branching characteristics: No lateral branches, flowering stems grow from a basal rosette.

Length of primary lateral branches: No lateral branches present, basal branching.

FOLIAGE

Leaf:

*Arrangement.*—Basal rosette.

*Leaflets.*—

*Shape.*—Trifoliate, broad ovate in outline.

*Quantity.*—Approximately 6 per basal rosette.

*Average length.*—8 cm.

*Average width.*—7.5 cm.

*Individual leaf blades.*—

*Shape of blade.*—Ovate.

*Apex.*—Short apiculate.

*Base.*—Acute to short attenuate.

*Margin.*—Biserrate.

*Texture of top surface.*—Very slightly glossy.

*Pubescence.*—Upper side sparsely covered with short adpressed hairs, average length: 0.5 mm, colored near RHS White N155D, main veins and secondary veins on under side moderately covered with short adpressed hairs, average length: 0.5 mm, colored near RHS Green-White 157D.

*Aspect.*—Leaf blades in an average angle of 75° to petiole.

*Color.*—Young foliage upper side: Near RHS Green 137B. Young foliage under side: In between near RHS Green 137B. Mature foliage upper side: Near RHS Green 137A. Mature foliage under side: Near RHS Green 137B.

*Venation.*—Type: Pinnate. Venation color upper side: Near RHS Yellow-Green 144B. Venation color under side: Near RHS Yellow-Green 144A.

*Petiole.*—Length: 18.5 cm. Diameter 0.2 cm. Color: Near RHS Green 137B, moderately tinged Greyed-Purple N186C. Texture: Densely covered with short hairs, average length: 1 mm colored near RHS White 155D.

*Stipule description (if present).*—Length: 1.1 cm. Diameter: 0.5 cm. Color: Near RHS Yellow-Green 144C. Texture: Densely covered with short hairs, average length: 1 mm, colored near RHS N155D.

FLOWER

Natural flowering season: Midsummer until Fall.

Days to flowering from rooted cutting: 9-12 months.

Inflorescence and flower type and habit: Inflorescence a terminal corymb, individual flowers rotate, single.

Rate of flower opening: 14 to 21 days from bud to fully opened flower.

Flower longevity on plant: Approximately one week.

Persistent or self-cleaning: Self-cleaning.

Bud:

*Shape.*—Broad ovate.

*Length.*—1.0 cm.

*Diameter.*—1.0 cm.

*Color.*—Near RHS Yellow-Green 147C.

Flower size:

*Diameter.*—5.5 cm.

*Depth.*—1.5 cm.

*Aspect.*—Upward and outward.

Tepals: No separate petals and sepals present, these floral structures are referred to as "Tepals" here.

*Quantity.*—5.

*Arrangement.*—Rotate.

*Length.*—3.3 cm.

*Width.*—2.7 cm.

*Shape.*—Obovate.

*Apex.*—Obtuse with 3 obtuse lobes.

*Base.*—Broad cuneate.

*Margin.*—Entire.

*Texture, upper and lower surfaces.*—Glabrous, matte, slightly velvety.

*Color.*—When opening, upper surface: Near RHS Purple 76A and 76B, lower section of petal flushed Purple 77A and 77B. Veins. Purple N79C. When opening, lower surface: Near RHS Purple-Violet N80D, lower section of petal flushed Purple-Violet N80B. Veins Purple-Violet N81B. Fully opened, upper surface: Near RHS Purple 76D. Base of petal has a large round blotch near Red-Purple N74D. Veins near Purple 77B. Fully opened, lower surface: Near RHS Purple 76C, heavily flushed Violet 84A and Purple 77A. Heavily veined Purple 77A.

Bracts (if present): No bracts present.

Longest peduncles:

*Length.*—20 cm.

*Diameter.*—5 mm.

*Angle.*—About 90° to basal rosette.

*Strength.*—Moderately strong.

*Texture.*—Slightly glossy, densely covered with short soft hairs, average length: 1 mm, colored near RHS N155D.

*Color.*—Near RHS Yellow-Green 147B, tinged Greyed-Purple N186C.

Shortest peduncles:

*Length.*—8 cm.

*Diameter.*—4 mm.

*Angle.*—About 35° to the peduncle.

*Strength.*—Moderately strong.

*Texture.*—Slightly glossy, densely covered with short soft hairs, average length: 0.7 mm, colored near RHS N155D.

*Color.*—Near RHS 147C.

Fragrance: No fragrance.

REPRODUCTIVE ORGANS

Stamens:

*Number.*—Average: 250.

Anthers:

*Shape.*—Narrow kidney-shaped to oblong.

*Length.*—Approximately 2 mm.

*Color.*—Near RHS Yellow-Orange 14B.

*Pollen.*—Color: Near RHS Yellow-Orange 14A. Quantity: Scant.

Pistil:

*Number.*—Average: 250.

*Length.*—3 mm.

*Style.*—Length: 2 mm. Color: Near RHS Yellow-Green 144B.

*Stigma.*—Shape: Linear. Color: Near RHS Yellow-Green 144C. Ovary Color: Near RHS Yellow-Green 144C.

OTHER CHARACTERISTICS

Seed/fruit: No seeds/fruits detected to date.

Temperature tolerance: Plants of the new *Anemone* are hardy to at least USDA Zone 6.

Diseases and pests: Neither resistance nor susceptibility to normal diseases and pests of *Anemone* has been observed.

What is claimed is:

1. A new and distinct cultivar of *Anemone* hybrid plant named 'MACANE002' as herein illustrated and described.

* * * * *